(12) United States Patent
Saji

(10) Patent No.: US 9,283,159 B2
(45) Date of Patent: Mar. 15, 2016

(54) 1-VINYLCYCLOHEX-3-ENE CARBALDEHYDE AND 4-VINYLCYCLOHEX-1-ENE CARBALDEHYDE FOR USE IN FLAVOUR AND ORAL CARE COMPOSITION

(71) Applicant: Givaudan SA, Vernier (CH)

(72) Inventor: Norikazu Saji, Kingston (GB)

(73) Assignee: GIVAUDAN SA, Vernier (CH)

( * ) Notice: Subject to any disclaimer, the term of this patent is extended or adjusted under 35 U.S.C. 154(b) by 0 days.

(21) Appl. No.: 14/373,207

(22) PCT Filed: Jan. 25, 2013

(86) PCT No.: PCT/EP2013/051396
§ 371 (c)(1),
(2) Date: Jul. 18, 2014

(87) PCT Pub. No.: WO2013/110739
PCT Pub. Date: Aug. 1, 2013

(65) Prior Publication Data
US 2014/0341821 A1 Nov. 20, 2014

(30) Foreign Application Priority Data
Jan. 26, 2012 (GB) .................................. 1201287.8

(51) Int. Cl.
| | | |
|---|---|---|
| A61K 8/33 | (2006.01) | |
| A61K 8/31 | (2006.01) | |
| A61K 8/34 | (2006.01) | |
| A61K 8/35 | (2006.01) | |
| A61Q 11/00 | (2006.01) | |
| A61K 8/92 | (2006.01) | |
| A23L 1/226 | (2006.01) | |

(52) U.S. Cl.
CPC ................. *A61K 8/33* (2013.01); *A23L 1/2265* (2013.01); *A61K 8/31* (2013.01); *A61K 8/34* (2013.01); *A61K 8/35* (2013.01); *A61K 8/922* (2013.01); *A61Q 11/00* (2013.01); *A23V 2002/00* (2013.01)

(58) Field of Classification Search
CPC .......... C07C 47/42; C07C 47/45; C07C 35/08
See application file for complete search history.

(56) References Cited

U.S. PATENT DOCUMENTS

| | | | |
|---|---|---|---|
| 4,465,695 A | * | 8/1984 | Mookherjee et al. .............. 426/3 |
| 2010/0204084 A1 | * | 8/2010 | Goeke et al. ..................... 512/22 |

FOREIGN PATENT DOCUMENTS

| | | |
|---|---|---|
| FR | 2183075 | 12/1973 |
| GB | 1372021 | 10/1974 |
| JP | S63126839 A | 5/1988 |
| WO | 2008005548 A2 | 1/2008 |
| WO | 2009021342 A2 | 2/2009 |

OTHER PUBLICATIONS

Merriam-Webster. Definition of "flavor". Retrieved from http://www.merriam-webster.com/dictionary/flavor.*
Hitti (2005). "Can You Smell Through Your Mouth?" WebMD. Retrieved from Http://www.webmd.com/brain/news/20050817/can-you-smell-through-your-mouth.*
International Search Report for PCT/EP2013/051396 dated Sep. 4, 2013.
Written Opinion for PCT/EP2013/051396 dated Sep. 4, 2013.
GB Search Report for GB1201287.8 dated Apr. 18, 2012.

* cited by examiner

*Primary Examiner* — Gollamudi Kishore
*Assistant Examiner* — Amanda Heyes
(74) *Attorney, Agent, or Firm* — Norris McLaughlin & Marcus PA

(57) ABSTRACT

Provided are oral care compositions comprising
a) at least one compound of formula (I)

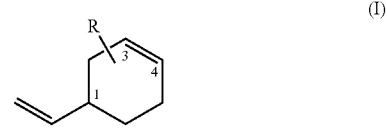

(I)

wherein R is carbonyl attached at C-1 or C-4; and
b) at least one mint flavor, for example, mint oil, menthol, l-carvone, l-limonene or menthone.
The compositions possess an enhanced mint flavor character.

4 Claims, No Drawings

1-VINYLCYCLOHEX-3-ENE CARBALDEHYDE AND 4-VINYLCYCLOHEX-1-ENE CARBALDEHYDE FOR USE IN FLAVOUR AND ORAL CARE COMPOSITION

This is an application filed under 35 USC 371 of PCT/EP2013/051396, which claims the priority benefit of GB 12101287.8 filed 26 Jan. 2012.

Provided are oral care compositions possessing an enhanced mint flavour character. There is further provided a method of enhancing the mint flavour character of an oral care composition, and the use of certain compounds to enhance the mint flavour character in oral care compositions.

Mint flavours of natural, nature-identical and synthetic origin, in particular peppermint and spearmint, or mixtures thereof, are popular flavours in oral care products, such as toothpaste, mouthwash and chewing gum, e.g to cover the taste of base ingredients and to impart a signal to a consumer that the product may deliver freshness and cleanliness upon use. Mint flavours are traditionally provided by adding mint oil to the oral care composition. Since these oils are of natural origin, the amounts available and thus the price may vary from year to year. In addition, to achieve remarkable mint flavour characteristics in an end-product, higher amounts of these natural oils are required, which increases the price.

The applicant has now found that, by the addition to a mint-flavoured oral care compositions of a compound selected from 4-vinylcyclohex-1-enecarbaldehyde and 1-vinylcyclohex-3-enecarbaldehyde, or a mixture thereof, the mint flavour perception may be enhanced, thus less mint flavour is required to achieve an essentially similar flavour character.

Thus, there is provided in one embodiment an oral care composition comprising a) at least one compound of formula (I)

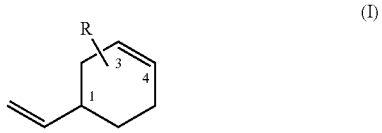

(I)

wherein R is carbonyl attached at C-1 or C-4; and b) at least one mint flavour, for example, mint oil, menthol, l-carvone, l-limonene or menthone.

The terms "mint flavour", "mint-flavoured" as used herein refer to substances possessing the characteristic flavour that is a property of extracts of certain plants, notably those of the Mentha family. Examples include peppermint (Mentha piperita), spearmint (Mentha spicata), Mentha arvensis, and Mentha cardiaca, and their hybrids and fractions.

However, some other plant species can provide similar flavour, and these are also comprehended. The characteristic flavour can also be obtained or imparted by the addition of at least one of a number of compounds, non-limiting examples including l-carvone, l-limonene, menthol and menthone, the last two-named of which constitute major constituents of mint oil.

In one embodiment the mint flavour is a mixture of two or more of natural mint oil, menthol, menthone l-carvone and l-limonene. The menthol may be either of natural origin or synthetic.

In a further embodiment, the mint flavour is derived from compounds that do not occur naturally, but which provide the characteristic flavour. These include Frescomenthe™, ethyl vanillin and ethyl maltol Suitable natural peppermint oils include, for example, Peppermint American Far West, Peppermint American Mid West, Peppermint American Willamette, Peppermint American Yakima, Peppermint Indian piperita, and the like. Suitable spearmint oils include, for example, Spearmint American Far West Native, Spearmint American Mid West Native, Spearmint Chinese Native, Spearmint Indian Native, and the like. Suitable Mentha arvensis oils include, for example, Peppermint Chinese Arvensis, Peppermint Indian Arvensis, Peppermint Chinese Terpenless, Peppermint Indian rectified, and the like. Suitable Mentha cardiaca oils include, for example, Spearmint American Far West Scotch, Spearmint American Mid West Scotch, and the like. In addition, synthetic mint oils, such as Spearmint supra and Peppermint supra, may also be used.

It has been found, that by addition of a compound of formula (I), or a mixture thereof, to a mint-flavoured composition, the amount of mint oil can be reduced by up to 10% by weight or even 15 to 20% by weight of the total amount of mint oil, compared to a composition essentially free of compounds of formula (I), without a noticeable change of the mint character. Furthermore, it was found that the admixture of a compound of formula (I), or mixtures thereof, impart a fresh cooling sensation, combined with some sweetening properties.

In one embodiment there is provided an oral care composition comprising a mint flavour and 4-vinylcyclohex-1-ene carbaldehyde.

In a further embodiment there is provided an oral care composition comprising a mint flavour and a mixture of 4-vinylcyclohex-1-ene carbaldehyde and 1-vinylcyclohex-3-ene carbaldehyde in the ratio of 1:99 to 100:0 (including, e.g., 1:9, 1:4, 1:2, 3:7, 2:3, 5:5, 3:2, 7:3, 4:1 and 9:1).

In a further embodiment there is provided an oral care composition comprising a mint flavour and a mixture 4-vinylcyclohex-1-ene carbaldehyde and 1-vinylcyclohex-3-ene carbaldehyde, said mixture comprising 0.1 to 99.9 weight % of 4-vinylcyclohex-1-ene carbaldehyde (such as 1%, 10%, 20% or 50%).

There is provided in a further embodiment an oral care composition comprising a) from about 0.01% to 5%, e.g. 0.1 to 5%, including 0.3 to 0.5% by weight of a flavour composition comprising mint flavour and b) about 0.05 to 10 ppm, such as about 0.1-5 ppm, including 1.5 ppm, 2 ppm, 3 ppm, of a compound of formula (I), or a mixture thereof.

The term "oral care composition" as used herein refers to non-food compositions that are designed to be taken into the mouth to deliver a variety of benefits. Such compositions include dentifrices, mouthwashes, mouth sprays and gargle compositions, breath strips (edible films placed in the oral cavity to administer thereto an active agent such as a flavourant or breath-freshening agent), and chewing gums. The term "dentifrice", as used herein, means toothpaste, oral care gels or liquids, unless otherwise specified. The dentifrice composition may be a single-phase composition or it may be a combination of two or more separate dentifrice compositions. The dentifrice composition may be in any desired form, such as deep-striped, surface-striped, multilayered, having the gel surrounding the paste, or any combination thereof.

There is provided in a further embodiment a method of providing an enhanced mint flavour to a mint-flavoured composition adapted to be received orally, comprising adding to said composition a compound selected from 1-vinylcyclohex-3-ene carbaldehyde and 4-vinylcyclohex-1-ene carbaldehyde, or a mixture thereof.

The disclosure is further described with reference to the following worked example, which describes a particular embodiment, and which is not intended to be in any way limiting.

EXAMPLE 1

1-Vinylcyclohex-3-ene carbaldehyde and 4-vinylcyclohex-1-ene carbaldehyde

The 500 mL flask was charged with crotonaldehyde (210.3 g, 3 mol), formaldehyde (270.0 g, 3.24 mol, 36% aqueous solution) and DMF (50 g, 0.68 mol). A cooled mixture of pyrrolidine (5.33 g, 0.075 mol) and propionic acid (5.56 g, 0.075 mol) was added with stirring during 5 minutes. This combined mixture was then slowly pumped with stirring into a heated (100° C.) autoclave that had been charged with a solution of 1,3-butadiene (570.4 g, 5 mol) in DMF (250 g, 3.42 mol). (Careful: a cold autoclave has to be charged with a cooled solution of butadiene in DMF, boiling point of butadiene: −4.5° C.). At this temperature, the internal pressure was 12.0 bar. During the first 3 h of this addition, the internal pressure slowly rose to 14.5 bar, while the temperature was kept at 100° C. The pressure then slowly dropped to 11.0 bar until the addition was finished after 4.5 hours. The reaction mixture was stirred at 100° C. for another 2 hours. After that time (the pressure was less than 8.1 bar) the reaction mixture was cooled to room temperature (by means of an internal cooling device) upon which the internal pressure dropped to less than 2 bar. The mixture was transferred to a 2.0 L separation funnel and diluted with hexane (620 g) and water (300 g) (Careful: excessive butadiene evaporates during this operation: use well ventilated hood). The upper layer was separated and washed successively with aq. acetic acid (50 ml) and water (50 ml) and then with sat. aq. sodium bicarbonate solution. The organic phase was dried with $MgSO_4$, filtered and concentrated under reduced pressure to furnish the crude product as a yellow oil (254 g) which was then distilled in vacuo over a 10 cm-Vigreux column (b.p. 47-72° C., 0.1 mbar), to yield 1-vinylcyclohex-3-ene carbaldehyde and 4-vinylcyclohex-1-ene carbaldehyde (189.9 g, 46.5%) in a ratio of about 2:1. The compounds may be separated by distillation or chromatography on silica gel under conditions known to the skilled person.

Taste description (5 ppm of the mixture in toothpaste base): green, herbal, fresh, citrus like, lightly minty, fatty, oily character, with some sweetness.

1-Vinylcyclohex-3-ene carbaldehyde: $^1$H-NMR (300 MHz, $CDCl_3$): 9.38 (s, 1H), 5.77-5.63 (m, 3H), 5.29 (d, J=10.6 Hz, 1H), 5.16 (d, J=17.7 Hz, 1H), 2.53-1.67 (m, 6H) ppm. $^{13}$C-NMR (75 MHz, $CDCl_3$): 201.8 (d), 137.9 (d), 127.1 (d), 123.9 (d), 117.0 (t), 51.7 (s), 29.4 (t), 26.9 (t), 22.0 (t) ppm. GC/MS (EI): 136 ($M^+$, 5), 118 (17), 107 (28), 91 (46), 79 (100), 67 (9), 53 (14), 39 (23).

4-Vinylcyclohex-1-ene carbaldehyde: $^1$H-NMR (300 MHz, CDCl3): 9.41 (s, 1H), 6.79 (bs, 1H), 5.81 (ddd, J=17.0, 10.2, 6.6 Hz, 1H), 5.04 (d, J=17.0 Hz, 1H), 4.99 (d, J=10.2 Hz, 1H), 2.55-2.05 (m, 5H), 1.91-1.83 (m, 1H), 1.44-1.30 (m, 1H) ppm. $^{13}$C-NMR (75 MHz, CDCl3): 194.0 (d), 150.1 (d), 142.0 (d), 141.3 (s), 113.5 (t), 37.1 (d), 32.0 (t), 27.2 (t), 20.8 (t) ppm. GC/MS (EI): 136 ($M^+$, 21), 121 (14), 107 (60), 91 (41), 79 (88), 67 (27), 54 (100), 39 (49). IR (neat, v/cm$^{-1}$): 2928s, 1686s, 1643m, 1420w, 1178w, 916w.

EXAMPLE 2

Flavour Compositions 2.1 Peppermint Flavour Composition

| Ingredient | parts per weight |
| --- | --- |
| Anethole | 8.00 |
| l-Menthol | 50.00 |
| Peppermint oil (*Mentha Arvensis*) | 26.40 |
| Eucalyptol | 5.00 |
| Herbal base | 0.45 |
| Lemon oil | 0.10 |
| Vanillin | 0.05 |
| Peppermint oil (*Mentha Piperita*) | 10.00 |

2.2 Peppermint Flavour Composition

| Ingredient | parts per weight |
| --- | --- |
| Anethole | 12.00 |
| l-Menthol | 55.00 |
| Peppermint oil (*Mentha Arvensis*) | 21.00 |
| Peppermint oil (*Mentha Piperita*) | 10.00 |
| Lemon oil | 0.45 |
| Vanillin | 0.05 |
| Herbal spicy base | 1.00 |
| Spearmint oil | 0.50 |

EXAMPLE 3

Mint Flavours 3.1 Spearmint Flavour

| Ingredient | parts per weight |
| --- | --- |
| Anethole | 10.00 |
| l-Menthol | 15.00 |
| Peppermint oil (*Mentha Arvensis*) | 7.00 |
| Eucalyptol | 1.00 |
| l-Carvone | 32.00 |
| Spearmint oil (*Mentha Cardiaca*) | 10.00 |
| Spearmint oil (*Mentha Spicata*) | 10.00 |
| Peppermint oil (*Mentha Piperita*) | 15.00 |
| 4-vinylcyclohex-1-ene carbaldehyde | 0.05 |

3.2 Peppermint Wintergreen Flavour

| Ingredient | parts per weight |
| --- | --- |
| Anethole | 12.00 |
| l-Menthol | 57.50 |
| Eucalyptol | 2.20 |
| Methyl Salicylate | 15.00 |
| Eugenol | 8.00 |
| Cinnamon base | 0.30 |
| Peppermint oil (*Mentha Piperita*) | 5.00 |
| 4-vinylcyclohex-1-ene carbaldehyde | 0.02 |
| 1-vinylcyclohex-3-ene carbaldehyde | 0.03 |

3.3 Fresh Peppermint Flavour

| Ingredient | parts per weight |
|---|---|
| Anethole | 9.00 |
| I-Menthol | 65.00 |
| Eucalyptol | 10.00 |
| Methyl Salicylate | 0.10 |
| Eugenol | 0.10 |
| I-Carvone | 0.80 |
| Peppermint oil (*Mentha Arvensis*) | 10.00 |
| Peppermint oil (*Mentha Piperita*) | 5.00 |
| Compound form Example 1 | 0.05 |

Peppermint Flavour

| Ingredient | parts per weight |
|---|---|
| Anethole | 10.00 |
| I-Menthol | 45.00 |
| I-Menthone | 10.00 |
| I-Menthyl Acetate | 5.00 |
| Peppermint Supra (Reconstituted Synthetic Peppermint) | 30.00 |

Spearmint Flavour

| Ingredient | parts per weight |
|---|---|
| Anethole | 8.00 |
| I-Menthol | 32.00 |
| Peppermint oil (*Mentha Arvensis*) | 14.00 |
| Peppermint oil (*Mentha Piperita*) | 5.00 |
| Eucalyptol | 1.00 |
| Peppermint Supra (Reconstituted Synthetic Peppermint) | 20.00 |

EXAMPLE 4

Application in Toothpaste

To a toothpaste base comprising 0.2 weight % saccharin, 1.0% of a flavour composition was added according to Table 1 below. For half of the samples the compound of Example 1 (1-vinylcyclohex-3-ene carbaldehyde and 4-vinylcyclohex-1-ene carbaldehyde (in a ratio of about 2:1; 1% in PG) was added.

TABLE 1

| | A | B | C | D | E | F |
|---|---|---|---|---|---|---|
| Mint flavour | Ex. 2.1 | Ex. 2.1 | Ex. 2.1 | Ex. 2.2 | Ex. 2.2 | Ex. 2.2 |
| Compound of Example 1 | — | 10 ppm | 5 ppm | — | 10 ppm | 5 ppm |

A piece of the thus-prepared toothpaste was put on a toothbrush and a panelist's teeth were brushed. Composition B in comparison to A was assessed to possessing a better freshness and composition C in comparison to A was assessed to give a more leafy natural American piperita character. The same results have been found for composition E and F in comparison to D.

EXAMPLE 5

Flavour Composition with Reduced Mint Oil

| Ingredient (parts per weight) | 4-1 | 4-2 | 4-3 |
|---|---|---|---|
| Herbal Base | 0.45 | 0.45 | 0.45 |
| Lemon oil | 0.10 | 0.10 | 0.10 |
| Vanillin | 0.05 | 0.05 | 0.05 |
| Anethole | 8.00 | 8.00 | 8.00 |
| I-Menthol | 50.00 | 50.00 | 50.00 |
| Peppermint oil (*Menthe Arvensis*) | 26.40 | 26.40 | 26.40 |
| Eucalyptol | 5.00 | 5.00 | 5.00 |
| Peppermint oil (*Mentha Piperita*) | 10.00 | 9.00 | 8.00 |
| Compound of Example 1* | — | 0.05 | 0.05 |
| Propylene Glycol (PG) | — | 0.95 | 1.95 |

*1-vinylcyclohex-3-ene carbaldehyde and 4-vinylcyclohex-1-ene carbaldehyde (in a ratio of about 2:1)

EXAMPLE 6

Application in Toothpaste

A toothpaste base comprising 0.2 weight % saccharin and 1.0 weight % of a flavour composition (Example 4: composition 4-1, 4-2 and 4-3 respectively) was prepared and assessed by panelists. No noticeable difference was observed between composition 4-1 and 4-2, and only a slight difference between composition 4-1 and 4-3 was observed. Composition 4-3 was described being slightly less impact and lacking the fullness of piperita leafy character.

The invention claimed is:
1. An oral care composition comprising
   c. at least one compound selected from the group consisting of: 4-vinylcyclohex-1-ene carbaldehyde and 1-vinylcyclohex-3-ene carbaldehyce; and,
   d. at least one mint flavour.
2. An oral care composition according to claim 1, wherein the mint flavour is selected from peppermint oil, spearmint oil, *Mentha arvensis* oil, menthol, l-carvone, l-limonene and menthone, and mixtures thereof.
3. An oral care composition according to claim 1 comprising 4-vinylcyclohex-1-ene carbaldehyde.
4. An oral care composition according to claim 2 comprising 4-vinylcyclohex-1-ene carbaldehyde.

* * * * *